United States Patent [19]

Groeger et al.

[11] Patent Number: 5,348,882
[45] Date of Patent: Sep. 20, 1994

[54] METHOD OF PRODUCING ENANTIOMERICALLY PURE, OPEN-CHAIN N-ALKYL-L OR D-AMINO ACIDS USING COMAMONAS TESTOSTERONI

[75] Inventors: Ulrich Groeger, Aschaffenburg; Karlheinz Drauz, Freigericht, both of Fed. Rep. of Germany

[73] Assignee: Degussa Aktiengesellschaft, Fed. Rep. of Germany

[21] Appl. No.: 885,878

[22] Filed: May 20, 1992

[30] Foreign Application Priority Data

May 24, 1991 [DE] Fed. Rep. of Germany ....... 4116980

[51] Int. Cl.$^5$ .................. C12P 41/00; C12N 9/80
[52] U.S. Cl. .................... 435/280; 435/228; 435/874
[58] Field of Search .......... 435/280, 228, 874

[56] References Cited

U.S. PATENT DOCUMENTS

| | | | |
|---|---|---|---|
| 3,945,888 | 3/1976 | Takahashi et al. | 195/29 |
| 5,120,652 | 6/1992 | Groeger et al. | 435/228 |
| 5,219,741 | 6/1993 | Groeger et al. | 435/107 |

FOREIGN PATENT DOCUMENTS 0416282  7/1990  European Pat. Off.
59-203494  11/1984  Japan.
6474987  3/1989  Japan.

OTHER PUBLICATIONS

Groeger U. et al., Angew Chem. Int Ed Engl 31:195-7 (1992).
Igloi K. et al., Proc. Hung. Annu. Meet. Biochem. 15:107-8 (1975) (abstract).
Jones, J., Tetrahedron 42:3351-3403 (1986).
Journal of the American Chemical Society 80:3349-55 (1958).

*Primary Examiner*—Douglas W. Robinson
*Assistant Examiner*—S. Saucier
*Attorney, Agent, or Firm*—Cushman, Darby & Cushman

[57] ABSTRACT

A method of producing enantiomerically pure, open-chain N-alkyl-L or D amino acids which can be carried out with good yields and without excessive or expensive purification and suitable for industrial production. A racemic mixture of an open-chain N-acyl-N-alkyl amino acid is split by means of a stereospecific amino acylase coordinated with an enantiomerically pure N-acyl-N-alkyl-L or D amino acid to yield one of the antipodes to the corresponding, enantiomerically pure, open-chain N-alkyl-L or D amino acid. Then, either the remaining initial compound or the cleavage product is separated. The enantiomerically pure, open-chain N-alkyl amino acids are useful, for e.g. cyclosporins.

3 Claims, No Drawings

METHOD OF PRODUCING ENANTIOMERICALLY PURE, OPEN-CHAIN N-ALKYL-L OR D-AMINO ACIDS USING COMAMONAS TESTOSTERONI

The present invention relates to a method of producing enantiomerically pure, open-chain N-alkyl L- or D-amino acids and enantiomerically pure N-alkyl amino acids with a free hydrogen or an acyl group on the nitrogen.

BACKGROUND OF THE INVENTION

Compounds of this type, preferably N-methyl amino acids, are e.g. components of cyclosporins. Cyclic peptides are involved which exhibit antibiotic and immunosuppressive action and for this reason are frequently used in tissue transplantations.

Racemates of these compounds can generally be produced in a purely chemical manner. However, the separation of these racemates into the individual enantiomers is very expensive and requires, e.g., chiral chromatographic columns. A further method of producing these enantiomerically pure compounds is via the free L- or D-amino acids, which are then subsequently alkylated to the α-amino group and optionally acylated.

However, a large number of byproducts is produced in this process which considerably reduce the yield and can often be removed only with great expense.

An enzymatic production of these compounds, e.g. by means of acylase, always has been unsuccessful in the past due to the unduly narrow substrate specificity of the acylases used. Acylase I is suitable, as described in The Journal of the American Chemical Society, 75, 918–920 (1953) and 111, 6354 to 6364 (1989), for the resolution of racemates of acylated α-amino acids insofar as the latter have a free hydrogen atom in the acylated amino group. The splitting then takes place L-specifically, so that the N-acyl-D-amino acid remains unsplit and can be separated, e.g., chromatographically or by means of precipitation from the L-amino acid produced: Acylase I, which can be isolated, e.g., from hog kidney or from Aspergillus, does exhibit a broad substrate specificity but no activity at all in the case of N-acyl-N-alkyl-DL-amino acids. Recently, other acylases have been found which have a specificity for terminal proline in peptides and to N-acyl proline as well as to cyclic N-acylatedamino acids modified from proline. These newer acylases are described in Japanese Patent Application 62-232381 (1987), "Biochimica et Biophysica Acta", 744 (1983, pp. 180–188 and in Published European Patent Application EP 0 416 282 A1. A substrate specificity to open-chain N-acyl-N-alkyl amino acids is not known for these acylases.

SUMMARY OF THE INVENTION

The object of the present invention is to provide a method of producing enantiomerically pure, open-chain N-alkyl-L- or D-amino acids which can be carried out with good yields and without excessive or expensive purification and which is suitable for industrial production.

The present invention provides a method of producing enantiomerically pure, open-chain N-alkyl-L or D-amino acids, in which a stereospecific amino acylase coordinated with an enantiomerically pure N-acyl-N-alkyl-L or D amino acid is allowed to act on a racemic, open-chain N-acyl-N-alkyl amino acid and the enantiomerically pure, open-chain N-alkyl amino acid obtained or the remaining enantiomerically pure N-acyl-N-alkyl amino acid is separated.

The present invention makes available a totally new method of obtaining enantiomerically pure, open-chain N-alkyl-amino acids which can also include an N-acyl group, depending on the product desired. The present method has the advantage that no screening of bacterial strains for the specially desired enantiomerically pure N-alkyl amino acid is necessary but rather the screening can be carried out with readily accessible N-acyl-Nalkyl amino acids. It is important in this connection that the screening substrate does not have a free H atom on the nitrogen, as is usually present in N-acylated amino acids (except proline). In addition to the open-chain compounds, heterocyclic compounds are also suitable if the one N-alkyl group is connected directly or via a heteroatom to the other N-alkyl group carrying the acid function. In particular, screening can be performed with such heterocyclic amino acids, preferably proline, and the enzyme obtained in this manner can be used for the stereospecific deacylating of open-chain N-alkyl-L,D amino acids. Since N-acylated proline, which is preferably enantiomerically pure for screening, is readily accessible and is a suitable screening substrate, the method of the invention makes possible a novel and very simple way of producing stereospecific, open-chain N-alkyl amino acids.

During the screening, the chemical compound is customarily used as the sole source of carbon and/or nitrogen in the nutrient medium, which source should be made accessible to an enzymatic reaction. At first, "enrichment cultures" are prepared and screened for microorganisms which can utilize the offered chemical compound for growth. After separation and purification of the various microorganisms by means of current microbiological techniques, the "pure cultures" obtained in this manner are recultivated, the cells washed and macerated, e.g. by mechanical treatment with a ball mill or by ultrasound. After separation of the cell fragments by centrifugation, a raw homogenate is obtained which should contain the desired enzyme.

In the present instance, the N-acyl-L-proline acylase known from EP 0 416 282 A1 was used to carry out the method, which can be obtained from *Comamonas testosteroni* DSM 5416 by screening with N-acetyl-L-proline as is described in detail in EP 0 416 282 A1.

It became apparent that this enzyme can be used for the production in accordance with the invention of enantiomerically pure, open-chain N-alkyl amino acids and thus makes them accessible in a simple manner, although the screening here was for a heterocyclic, N-acetylated amino acid. It is especially significant in this connection that the amino acylase does not have to be evaluated with the corresponding open-chain N-acyl-N-alkyl amino acids during the screening but rather can also be evaluated with N-acyl proline without the substrate specificity then excluding the corresponding open-chain amino acids. Thus, in particular, proline acylases which are known or have been newly found by screening can be used for the method of the invention.

On the other hand, other acylases can also be used for the method of the invention which are obtainable by screening with other simple molecules such as:

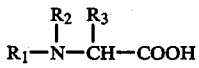

in which

R₁=COCH₃; COCH₂Cl
R₂=CH₃; C₂H₅; C₃H₇
R₃=H; CH₃; CH₃-CH₂-CH₃; CH₂-C(CH₃)H-CH₂;
CH₃-CH-CH₂-CH₃; CH₂-OH; HO-CH-CH₃;
CH₂SH; CH₂-CH₂-SCH₃;
CH₂COOH; CH₂-CH₂-COOH;
CH₂-CONH₂; CH₂-CH₂-CONH₂;
CH₂-CH₂-CH₂-CH₂-NH₂;

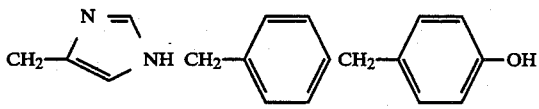

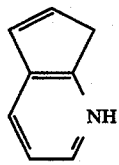

Normally, L-specific acylases are sought and used for carrying out the method since they are usually more readily obtainable. The corresponding N-alkyl-D-amino acids can then be readily obtained by means of chemical hydrolysis (deacylation) of the remaining, enantiomerically pure N-acyl-N-alkyl-D-amino acid. The deacylation can be carried out according to methods known in the literature chemically in an acidic or alkaline environment with retention of the configuration to the corresponding, enantiomerically pure N-alkyl amino acid.

DETAILED DESCRIPTION OF PREFERRED EMBODIMENTS

The method of the invention will be explained in detail using the following examples.

EXAMPLE 1

Determination of activity of acylase
Hydrolysis of N-chloroacetyl-N-methyl-L-alanine
1 ml of a 30 mM solution of N-choloracetyl-N-methyl-L-alanine in 0.1M tris-HCl₁, pH 7.0 was introduced into a reaction container thermostatted to 30° C. and mixed with 1.99 ml 0.1M tris —HCl pH 7.0. The reaction was started by adding 0.01 ml N-acyl-L-proline acylase from Comamonas TESTOSTERONI DSM 5416 corresponding to 0.23 units and 0.2 μg protein. 1 unit is defined as the amount of enzyme which converts 1 μmole of N-acetyl-L-proline per minute at 30° C. and pH 7.0. Specimens were taken at various points in time to detect the course of the reaction, compounded with 2N HCl 1:2 and subsequently analyzed by HPLC using an RP 8-column (250×4 mm). After elution with 7% (v/v) acetonitrile in 0.01M heptane sulfonic acid (adjusted to pH 2.2 with 85% H₃PO₄) at a flow rate of 2.2 ml/min. and a column temperature of 40° C., the decrease of N-chloroacetyl-N-methyl-L-alanine was determined by measuring the UV absorption at 210 nm.

After a reaction time of 60 minuthes, the conversion was 100%.

EXAMPLE 2

Hydrolysis of N-chloroacetyl-N-methyl-D,L-alanine
The procedure of Example 4 was repeated. However, the reaction mixture contained 1 ml of a 60 mM solution of N-chloroacetyl-N-methyl-D,L-alanine in 0.1M tris-HCl, pH 7.0, 1.98 ml 0.1M tris HCl, pH 7.0 and 0.02 ml enzyme corresponding to 0.46 units and 0.4 μg protein. After a reaction time of 60 minutes, the conversion was 42%, and after 120 minutes, the conversion was 43%. The enantiomeric purity of the N-methyl-L-alanine was determined, after coversion to the N-trifluoromethyl ester derivative, to be ≧89% (ee).

EXAMPLE 3

Hydrolysis of N-chloroacetyl-N-methyl-D,L-2-aminobutyric acid
The procedure described in Example 4 was repeated. However, the reaction mixture contained 1 ml of a 60 mM solution of N-chloroacetyl-N-methyl-D,L-2-amino butyric acid in 0.1M tris-HCl, pH 7.0, 1.90 ml 0.1M tris-HCl, pH 7.0 and 0.10 ml enzyme corresponding to 2.3 units and 2 μg protein. After a reaction time of 60 minutes, the conversion was 46% and after 120 minutes, the conversion was 49%.

EXAMPLE 4

Substrate specificity of N-acyl-L-proline acylase in relation to various N-acyl-N-alkyl-D,L amino acids
The same method described in Examples 1 and 2 was used and the relative activity of the enzyme in relation to various N-acyl-N-alkyl-D,L amino acids determined. Table 1 shows the result.

TABLE 1

| Substrate (20 mM) | Activity (%) |
| --- | --- |
| N—ClAc—N-methyl-D,L-alanine | 100 |
| N—ClAc—N-ethyl-D,L-alanine | 71 |
| N—ClAc—N-propyl-D,L-alanine | 23 |
| N—ClAc—N-methyl-D,L-2-amino butyric acid | 9 |
| N—ClAc—N-ethyl-D,L-2-amino butyric acid | 2 |

What is claimed is:

1. A method of separating enantiomers of N-acyl-N-alkyl-amino acids comprising:
   subjecting an enantiomeric mixture of open-chain N-acyl-N-alkyl amino acids to the action of a stereospecific N-acyl-L-proline acylase derived from *Comamonas testosteroni* and
   separating the enantiomerically enriched, open-chain N-alkyl-L-amino acid obtained or the remaining enantiomerically enriched N-acyl-N-alkyl-D-amino acid.

2. A method as set forth in claim 1 in which an L-specific N-acyl-proline acylase from *Comamonas testosteroni* DSM 5416 is used.

3. A method as set forth in claim 6 or 12 further including the step of deacylating the remaining, enantiomerically enriched N-acyl-N-alkyl-D-amino acid.

* * * * *